(12) United States Patent
Javadi et al.

(10) Patent No.: US 10,571,386 B2
(45) Date of Patent: Feb. 25, 2020

(54) METHOD AND APPARATUS FOR DETECTION AND MEASUREMENT OF PARTICLES WITH A WIDE DYNAMIC RANGE OF MEASUREMENT

(71) Applicant: Stratedigm Inc., San Jose, CA (US)

(72) Inventors: Shervin Javadi, Monte Sereno, CA (US); Arjuna Ragunath Karunaratne, Fremont, CA (US)

(73) Assignee: Stratedigm, Inc., San Jose, CA (US)

( * ) Notice: Subject to any disclaimer, the term of this patent is extended or adjusted under 35 U.S.C. 154(b) by 15 days.

(21) Appl. No.: 15/791,199

(22) Filed: Oct. 23, 2017

(65) Prior Publication Data
US 2018/0045637 A1 Feb. 15, 2018

Related U.S. Application Data

(62) Division of application No. 14/332,347, filed on Jul. 15, 2014, now Pat. No. 9,857,284.

(60) Provisional application No. 61/957,887, filed on Jul. 15, 2013.

(51) Int. Cl.
*G01N 15/14* (2006.01)

(52) U.S. Cl.
CPC ..... *G01N 15/1429* (2013.01); *G01N 15/1459* (2013.01); *G01N 2015/145* (2013.01); *G01N 2015/1493* (2013.01)

(58) Field of Classification Search
CPC .............. G01N 15/1429; G01N 15/14; G01N 15/1459; G01N 2015/145; G01N 2015/1493; G01N 2015/1439
See application file for complete search history.

(56) References Cited

U.S. PATENT DOCUMENTS

| | | | |
|---|---|---|---|
| 4,596,036 A | 6/1986 | Norgren et al. | |
| 5,798,827 A * | 8/1998 | Frank | G01N 15/1459 356/336 |
| 6,713,019 B2 | 3/2004 | Ozasa et al. | |
| 7,362,421 B2 * | 4/2008 | Pan | G01P 5/26 356/28.5 |
| 7,362,432 B2 * | 4/2008 | Roth | B82Y 10/00 250/458.1 |
| 7,385,682 B2 | 6/2008 | Chu et al. | |
| 7,561,267 B2 | 7/2009 | Luo et al. | |

(Continued)

FOREIGN PATENT DOCUMENTS

WO 2013181453 A2 12/2013

OTHER PUBLICATIONS

Smith, Steven W., *The Scientist & Engineer's Guide to Digital Signal Processing*, 1st edition, 1997, Chapter 17, pp. 297-310, http://www.dspguide.com/ch17/2.htm.

*Primary Examiner* — Gordon J Stock, Jr.
(74) *Attorney, Agent, or Firm* — Kilpatrick Townsend and Stockton LLP

(57) ABSTRACT

Light from a light source is directed at a flow path of particles of a flow cytometer. The directed light results in a light pattern having a plurality of lobes. A first signal is detected exceeding a first threshold. A second signal exceeding a second threshold is detected, wherein the second threshold is greater than the first threshold. Based on detecting the second trigger after detecting the first trigger, is determined that the first and second signals were created by a relatively large particle.

14 Claims, 8 Drawing Sheets

(56) References Cited

U.S. PATENT DOCUMENTS

| | | | | |
|---|---|---|---|---|
| 8,350,231 | B2 * | 1/2013 | Muraki | G01N 15/1429 |
| | | | | 250/459.1 |
| 8,497,989 | B2 * | 7/2013 | Imai | G01N 15/1429 |
| | | | | 356/338 |
| 8,570,500 | B2 | 10/2013 | Javadi et al. | |
| 9,291,562 | B2 * | 3/2016 | Hell | G01N 21/645 |
| 9,719,855 | B2 * | 8/2017 | Arab | G01N 15/1463 |
| 9,857,284 | B1 * | 1/2018 | Javadi | G01N 15/1459 |
| 10,001,434 | B2 * | 6/2018 | Kaduchak | G01N 15/1012 |
| 10,024,780 | B2 * | 7/2018 | Shah | G01N 15/1429 |
| 2003/0048433 | A1 * | 3/2003 | Desjonqueres | G01N 21/53 |
| | | | | 356/73 |
| 2003/0142289 | A1 * | 7/2003 | Ortyn | G01N 15/1012 |
| | | | | 356/28 |
| 2008/0037004 | A1 | 2/2008 | Shamir et al. | |
| 2009/0071225 | A1 * | 3/2009 | Schilffarth | G01N 15/1012 |
| | | | | 73/1.02 |
| 2014/0268143 | A1 * | 9/2014 | Tropea | G01N 15/0211 |
| | | | | 356/342 |
| 2016/0238510 | A1 * | 8/2016 | Bachalo | G01N 15/1429 |
| 2017/0276594 | A1 * | 9/2017 | Pariseau | G01N 15/1459 |
| 2019/0235222 | A1 * | 8/2019 | Ryu | G02B 21/06 |

* cited by examiner

METHOD AND APPARATUS FOR DETECTION AND MEASUREMENT OF PARTICLES WITH A WIDE DYNAMIC RANGE OF MEASUREMENT

CROSS-REFERENCES TO RELATED APPLICATIONS

This application is a divisional of U.S. Non-Provisional application Ser. No. 14/332,347, filed Jul. 15, 2014, and also claims the benefit of U.S. Provisional Application No. 61/957,887, filed Jul. 15, 2013, which is incorporated by reference.

BACKGROUND OF THE INVENTION

In a flow cytometer, a focused light source such as a laser beam or LED is arranged to shine on particles flowing within a fluid stream. The particles scatter the light and also cause fluorescent light of a different wavelength than the incident beam to be emitted.

The focused spot however is usually not a bright point that decays away monotonically in all directions. Rather, the beam from the light source such as a laser can have "lobes." The far field of the beam is typically the Fourier transform of the laser aperture. Thus, for example a square aperture will give a far field which is a 2 dimensional Sync function as shown in FIG. 1. The beam shaping optical elements may also have small reflections from various surfaces as shown in FIG. 3, coatings can reduce the reflections but typically will not completely eliminate them. Both of these effects have the net effect of causing the laser beam in the flow channel 17 to have a main peak 3 flanked on one or both sides by many smaller peaks 4 as shown in FIG. 3 and FIG. 2.

While the power in a laser minor side lobe 4 is typically 1% or less of the main lobe 3, a difficulty arises when very large particles 20 and very small particles 21 as shown in FIG. 2 are mixed. A large particle passing over a minor lobe of the laser will cause an amount of signal that is comparable to a small particle that is passing the main lobe of the laser. A large particle passing over a minor lobe of the laser and then subsequently passing over the main lobe of the laser can incorrectly be counted as a small particle followed by a large particle.

BRIEF SUMMARY OF THE INVENTION

This invention relates to the field of cytometry. It is sometimes necessary to detect particles of widely varying size, typically from 50 nm to 50 µm a dynamic range of 1000×. According to many embodiments, particle parameter measurement which may be recalculated instantaneously or at a later time, dependent on the determination as to if the particle was a large or small particle.

Many embodiments relate to an analog or digital deconvolution filter that can operate on a light intensity data pattern received from light emissions in a flow channel, so as to mitigate the effect of the laser lobes or other stray light in the flow channel caused by optical reflections or imperfections.

Many embodiments relate to a particle detection trigger mechanism that may be retriggered or restarted depending on measured values of data reaching fulfilling certain conditions requiring restart.

Many embodiments relate to a detection system in which laser light is directed at a flow path of particles of a flow cytometer. The laser light results in a light pattern having a plurality of lobes. A first signal is detected exceeding a first threshold. A second signal exceeding a second threshold is detected, wherein the second threshold is greater than the first threshold. Based on detecting the second trigger after a particular time point after detecting the first trigger, is determined that the first and second signals were created by a single relatively large particle.

DETAILED DESCRIPTION OF THE INVENTION

Figure 4:
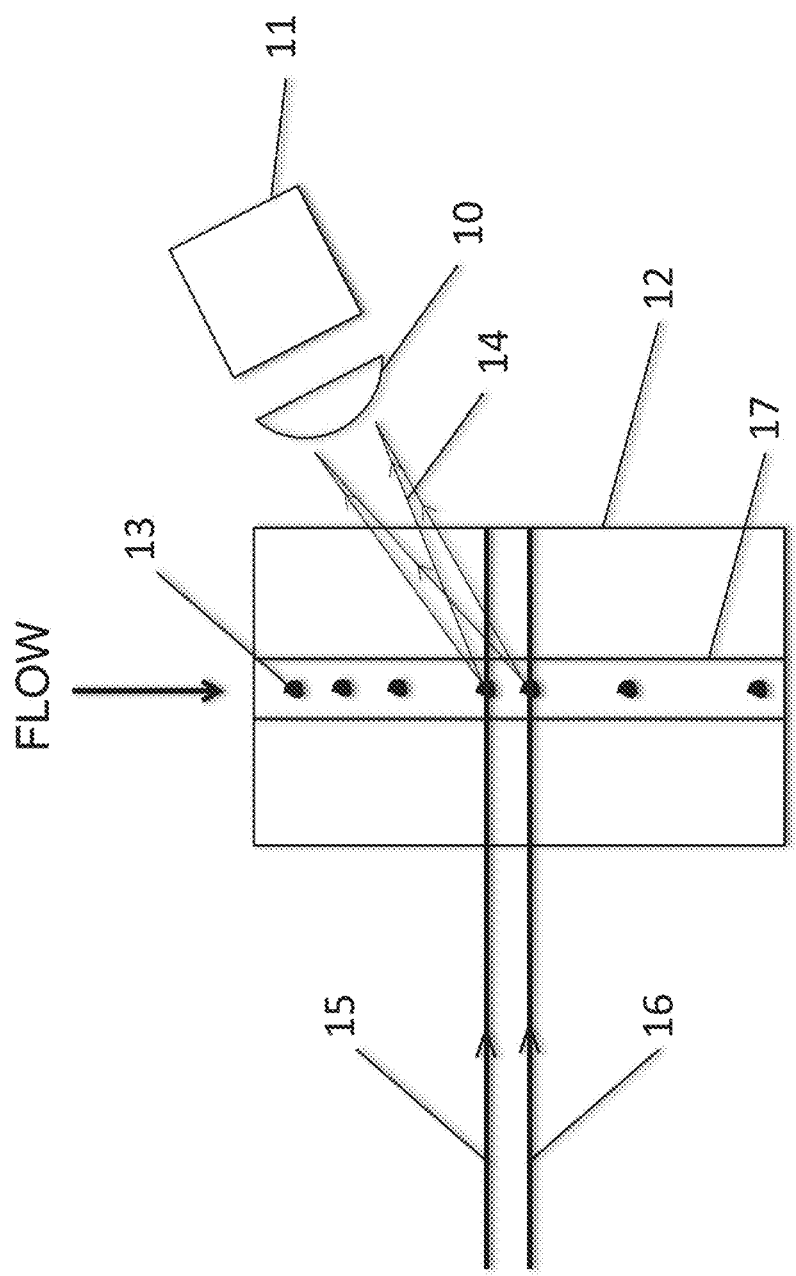
FIG. 4 is a drawing of two laser beams of different colors intersecting a flow channel, according to many embodiments.

In most cases, flow cytometers operate by flowing particles inside a small channel 17 formed in a middle of typically a quartz cuvette 12 as shown in FIG. 4. In most cases the surfaces of quartz surfaces forming the inside of the cuvette and the outside of the cuvette are highly polished and flat such that a laser beam may be shone through and focused at one point in the cross section of the channel with optical precision. The particles flowing past the light source, such as a laser beam then cause scattered light emissions of the same wavelength of the laser, or fluorescent light emissions of a higher wavelength than of the laser. These light pulses are detected by one or more light detectors 11 such as Photomultipliers or Photodiodes with filters that only pass the wavelength(s) of interest. The pulsations last an amount of time determined by the flow rate in the channel and the size of the particle and the width of the laser spot. The time domain waveform of the scattered or fluorescent light being the convolution of the spatial distribution of the scattering or fluorescent emission of the particle with the spatial distribution of the laser light pattern, the convolution being done at a rate determined by the flow rate.

For simplistic analysis let us first consider a "Particle A" having an impulse as the spatial distribution of 0,1,0. It can be seen that if we convolve this particle pattern with a "Laser A" having an impulse spatial distribution of 0,1000,0 the resulting signal is 0,1000,0. Similarly if we convolve a "Laser B" with spatial distribution 0,1,0 with a "Particle B" of impulse spatial distribution 0,1000,0, the resultant signal is 0,1000,0. In this simple example, both cases cause an identical and indistinguishable signature of emitted light. In a more realistic case a particle that scatters more may be larger and have a wider spatial signature such as 0,0,1,10, 100,1000,100,10,1,0,0.

Figure 1:
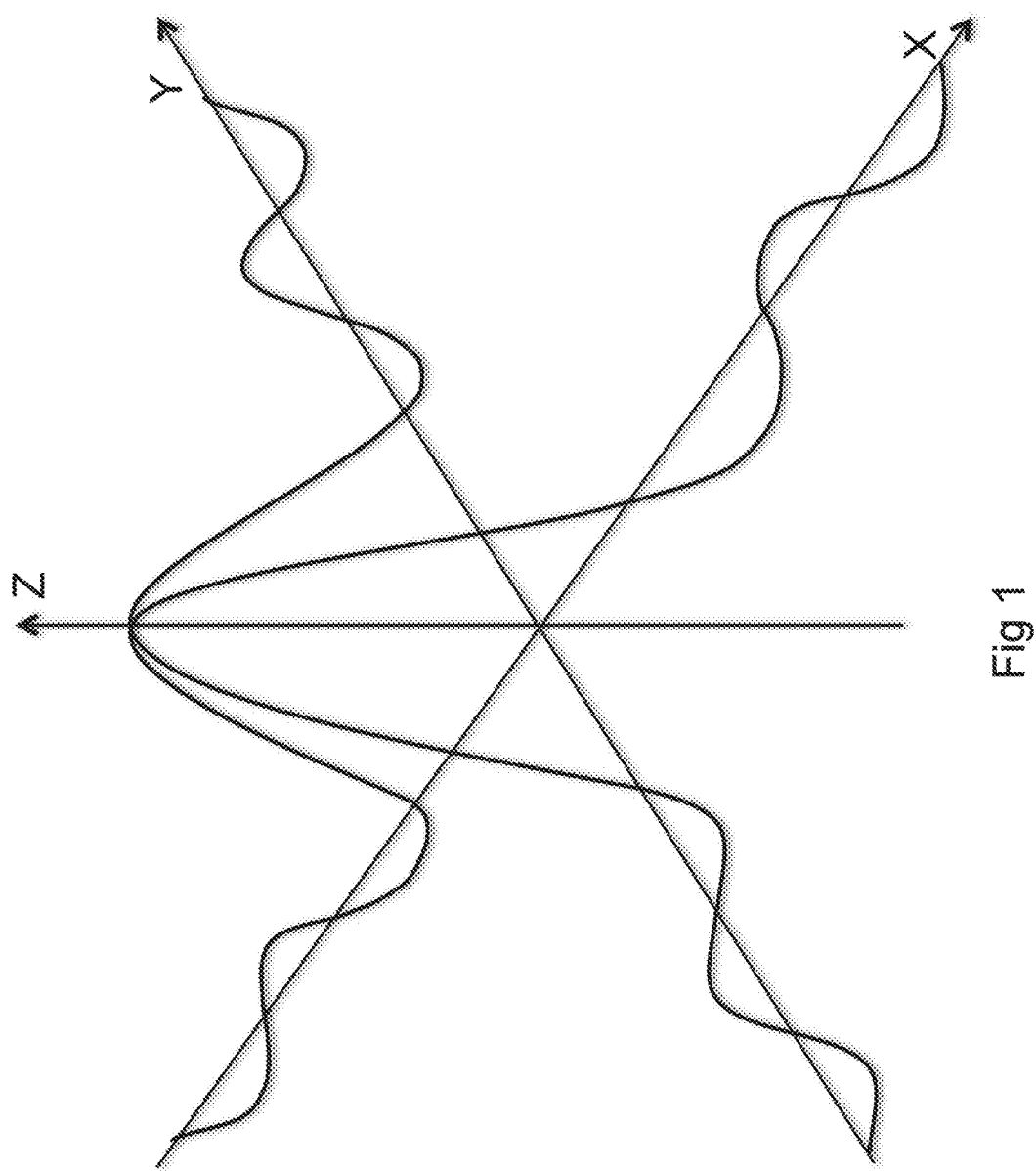
FIG. 1 is a drawing of a two dimensional Sync function.
Figure 2:
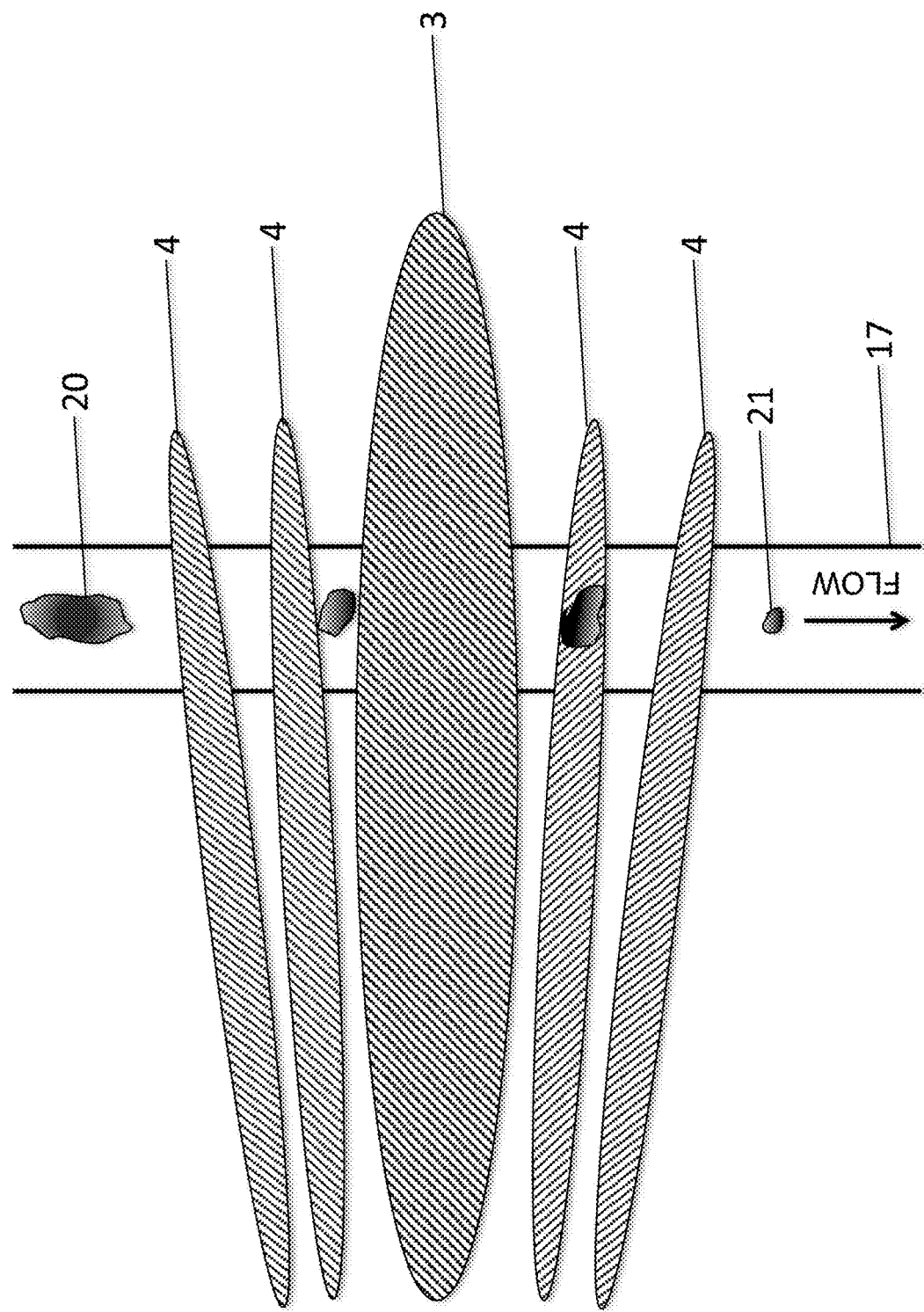
FIG. 2 is a drawing of the light pattern intersecting the flow channel.

A problem occurs when the laser spot spatial intensity variation in the cuvette is not an impulse, but instead is non-monotonically decaying undulating waveform as shown in FIG. 1 and FIG. 2. Such undulations are quite natural. It is well known that the far field of a laser or in general any source of electromagnetic radiation, is the Fourier transform of the spatial distribution of the electromagnetic energy at its emission aperture. The mathematical summation of the phase shifted energy received at a distant point (far field) from each emission point being mathematically equivalent to a Fourier transform. Thus, for example a uniform square emission aperture will yield a Sync function in X and in Y. A round aperture will yield a Bessel function. Both of the above functions have "Minor Lobes" in the far field with zeros in between the lobes.

Figure 3:
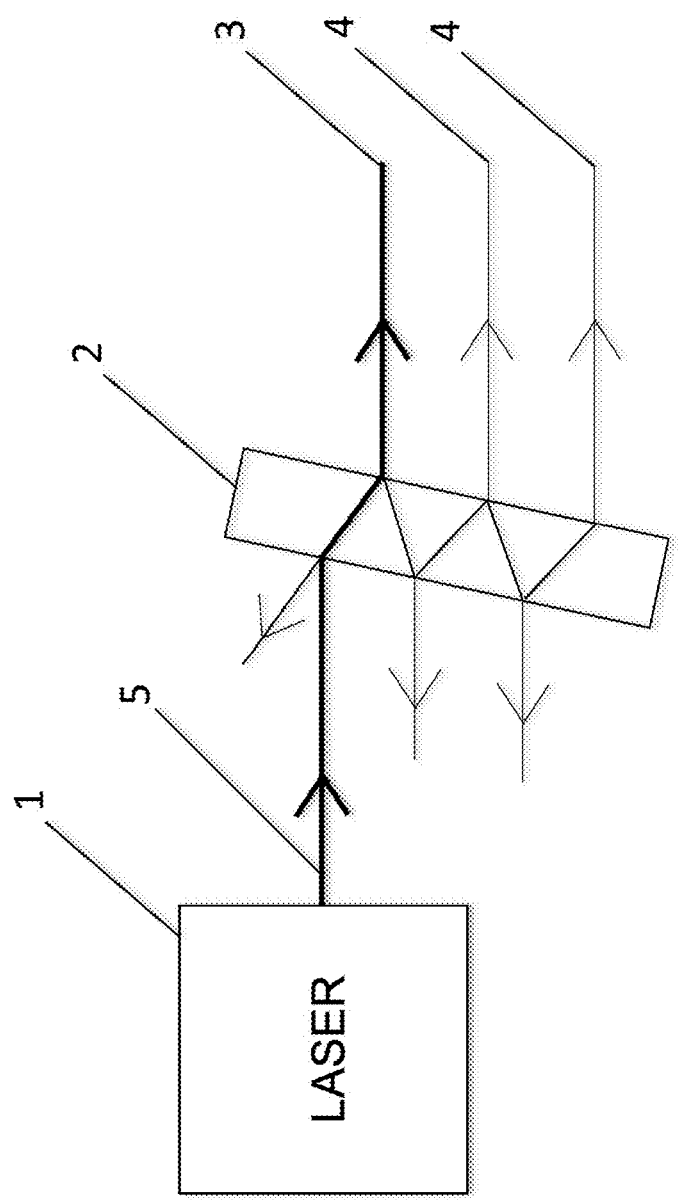
FIG. 3 is a drawing of secondary lobes being created by reflections from optical elements.

Minor laser lobes or their equivalent can also be created by near normal incidence of a laser beam 5 to an optical element 2 as shown in FIG. 3, due to reflected beams 4 in addition to the main beam 3. Imperfections in the light path can also cause minor lobes. Anti-reflective coatings can reduce the reflection but not eliminate it, especially in the case of simultaneous presence of multiple laser emission sources of different wavelengths, where the coating must necessarily be a compromise.

Typically as shown in FIG. 4 several laser beams of different colors 15, 16 are arranged along the flow path and optical element(s) 10 are used to capture any emitted light 14 as the particle flows past each of the laser beams 15 and 16. Thus, the light from any laser and its lobes will cause an electrical signal output from a photo-detector as long as it is of a wavelength that is allowed to reach the photo-detector. Different optical architectures can minimize this effect by using designed including but not limited to pinholes or to limit the amount of light collected away from the center of the laser but these designs do not block all of the light emitted by the laser light outside of a specified region.

Considering a flow cytometry system with a single laser and nearby side-lobes: First consider a "Particle A" with a spatial pattern that is an impulse of 0,1,0 convolved with a "Laser C" of spatial pattern 0,1,0,1000,0,1,0 (the ones on either side of the 1000 being the side lobes), the convolution yields 0,1,0,1000,0,1,0. Now consider a "Particle B" with a spatial pattern of 0,1000,0, convolved with the same laser pattern for "Laser C" the convolution yields 0,1000,0, 1000000,0,1000,0. With a triggering threshold of 1000, one can detect the particle with the spatial pattern of 0,1,0 correctly, however, one will falsely detect the response to the lobe only for the particle with a spatial pattern of 0,1000,0, further, these particles may be "aborted" completely with a low trigger level because they may be classified as "doublets"—i.e. the presence of two particles in the laser beam simultaneously. In certain applications, it can be necessary to be able to distinguish between small particle entering the main lobe and a "larger" particle entering a side lobe. As used herein, the term "larger" not necessarily meaning physically larger but instead could be a particle of the same size but with more fluorescence or scattering.

Certainly a physically larger "Particle C" can have a spatial pattern like 0,0,1,10,100,1000,100,10,1,0,0 which indicates a relatively large physical size. Convolution of this particle with a "Laser C" with pattern 0,1,0,1000,0,1,0, yields 1,10,1100,11000,100101,1000000,100101,11000, 1100,10,1 in which case the output signal is monotonically increasing and decreasing with a single peak even though the laser lobes are non-monotonic.

Depending on the spatial distribution of the laser and the spatial distribution of the particle, and the relative sizes of the light lobes compared to the particle size, it is possible for a single particle to create several blips that may be mistakenly interpreted as several different particles.

With knowledge of the laser lobe structure within the cuvette it is possible to mitigate the effect of the lobes. The essence of this method is "deconvolution" of the spatial distribution of the scattering or fluorescent emission of the particle with the spatial distribution of the laser light pattern.

Figure 5:
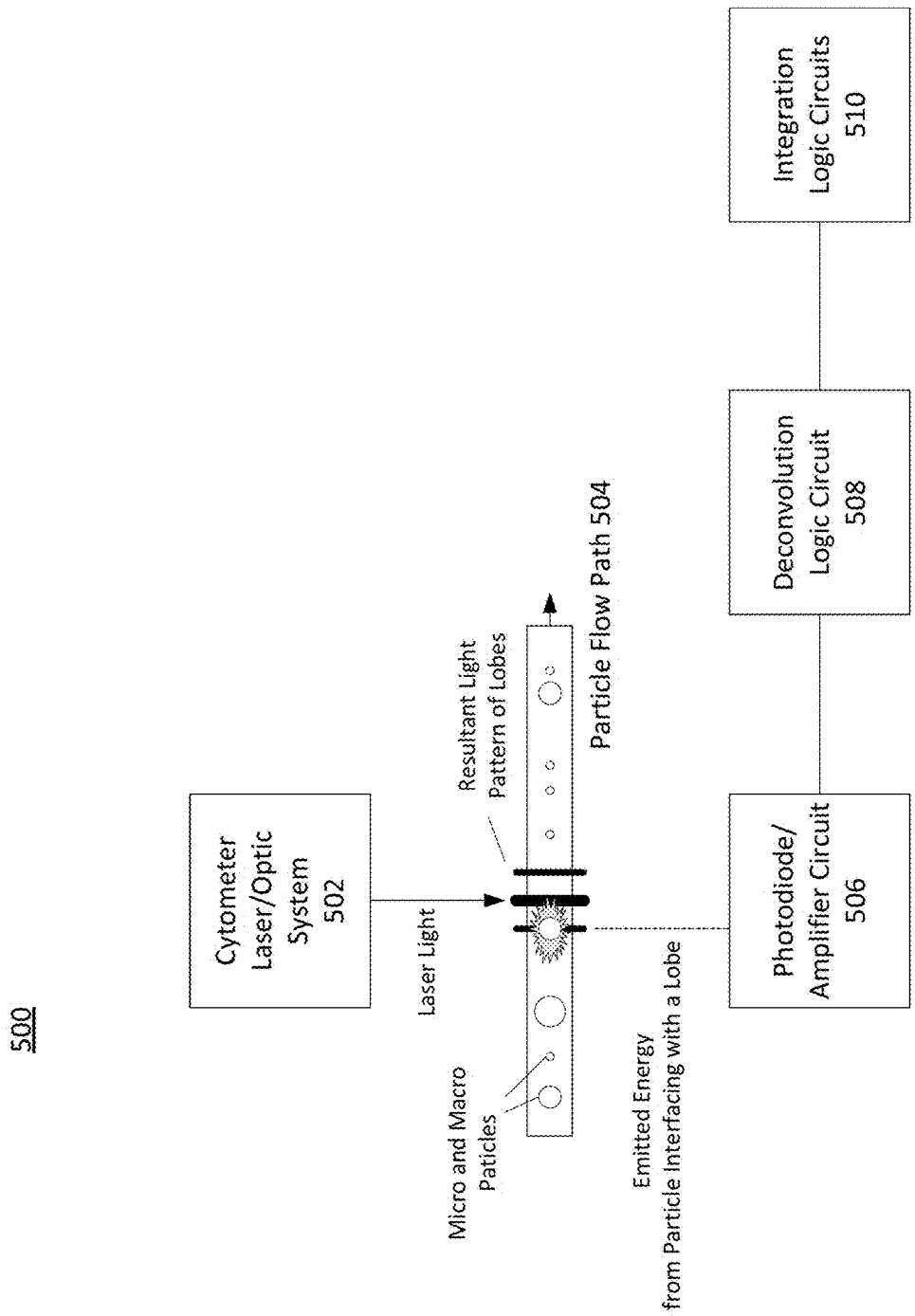
FIG. 5 is a system diagram of a flow cytometer system, according to many embodiments.

In an analog cytometer system 500 as shown at FIG. 5, (having a laser system 502, flow path 504, photodiode/amplifier circuit 506, integration logic circuits 510 with analog integrators and the like). An exemplary flow cytometer system is disclosed at U.S. Pat. No. 8,570,500, which is incorporated by reference. By way of example but not limited to: Having knowledge of the relative amplitudes and positions of the main and side lobes it is possible to create a deconvolution logic circuit 508, by way of example having two analog comparators within one set to the actual trigger threshold desired for detection of all particles, and another set somewhat higher.

The logic 508 will classify any trigger event on the lower trigger, only when followed by a trigger on the higher trigger at a time separated by the distance of the laser lobes, to be a false first trigger of a large particle entering a side lobe, and requiring an immediate restart of the integrators based on the higher trigger level, since the higher trigger indicates a large particle in the main lobe of the laser, and not a side lobe. Comparatively, a smaller particle would not trigger on the high trigger on the side lobe, because the energy provided by the side lobe is not high enough to trigger the lower trigger, but only trigger at the main lobe.

Typically reset of integration logic 510 for determination of peak height and area is not required because the side lobe energy is so low that the main lobe can be integrated right on top of the side lobe integration, which started based on the lower trigger just previously, with less than 1% error. However, calculations such as width, which is determined by integrating a constant current onto a capacitor for the duration of the pulse, can require restart of the integration.

Figure 7:
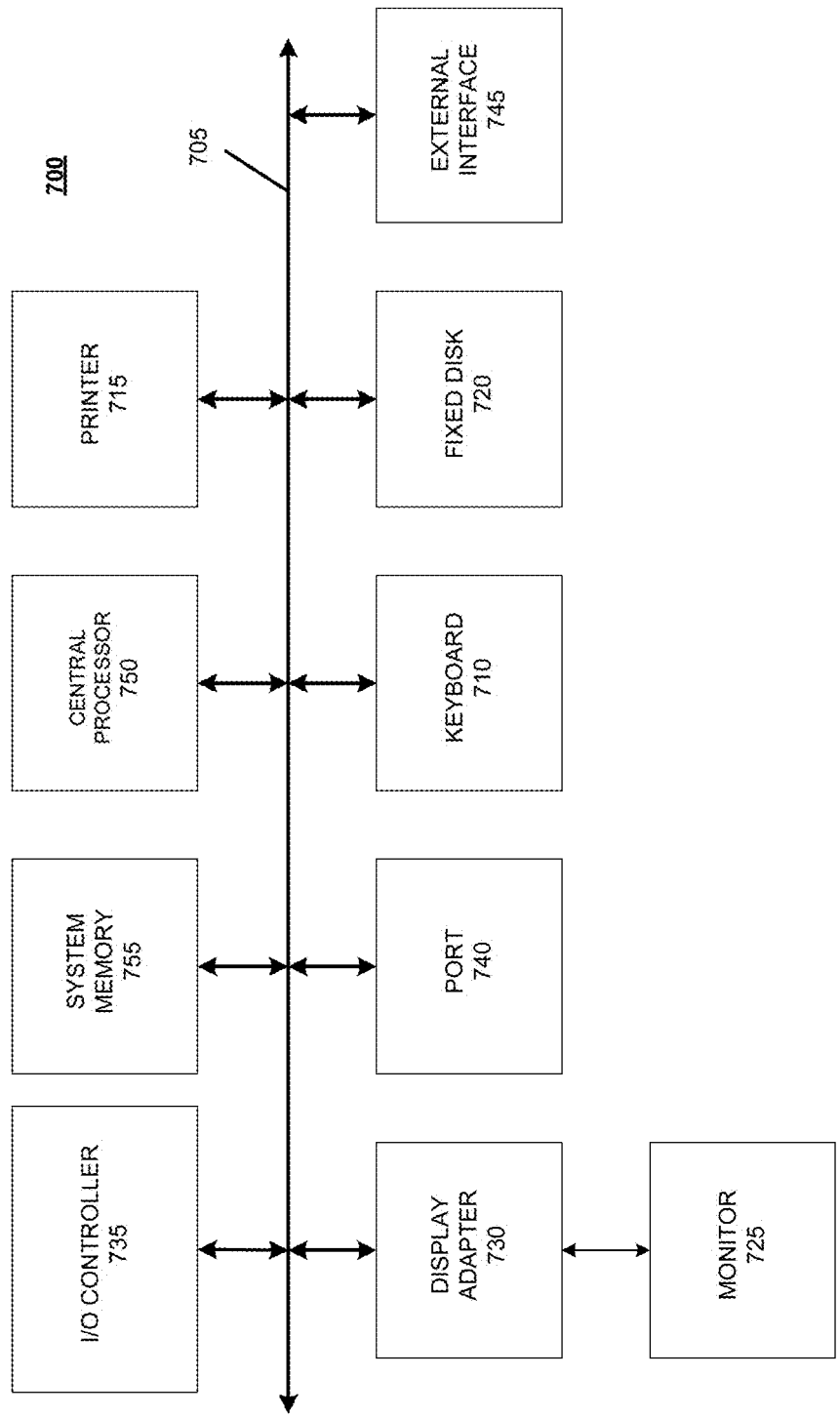
FIG. 7 is a system diagram of a computing system, according to many embodiments.

Alternatively, for a digital cytometer system where the entire data stream is digitized it is possible to process captured data through an inverse deconvolution filter by way of a processor shown at FIG. 7. An exemplary deconvolution filter is disclosed by Steven W. Smith, The Scientist & Engineer's Guide to Digital Signal Processing, 1st edition (1997), (e.g., Chapter 17), which is incorporated by reference in its entirety. Here, spatial convolution is occurring between two spatial patterns that yields a time domain signal. One of the spatial patterns is the light (laser) emission pattern. The other spatial pattern is the emitted energy pattern of the particle. Hence, $L(x)*P(x) \Rightarrow S(t)$ where $L(x)$ is the laser spatial pattern (spatial meaning in the dimension x), * is the convolution integral, $P(x)$ is the particle spatial pattern, and $S(t)$ is the time domain signal received. Accordingly, knowing $L(x)$ and $S(t)$ the signal can be deconvoluted. This can be done prior to processing any parameters for the received pulse such as Peak, Area, Log Area, Log peak, Width, etc.

Figure 6A:
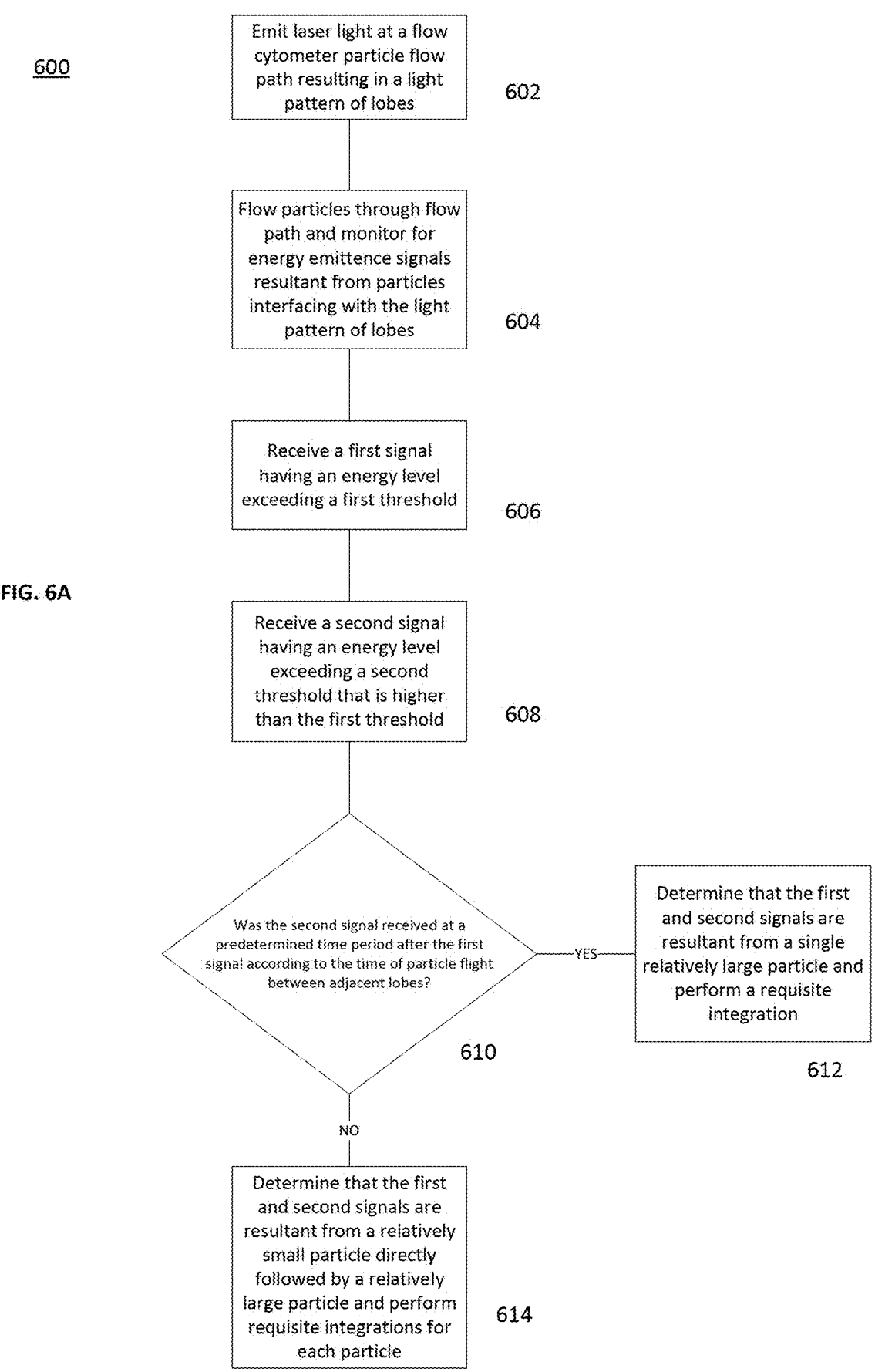
FIGS. 6A and 6B are flow charts of methods for detecting a particle, according to many embodiments.

FIG. 6A shows a flow chart of a method 600 that can be implemented by way of an analog system per FIG. 5. At operation 602, laser light is emitted at a flow cytometer particle flow path resulting in a light pattern of lobes. Generally, a main center lobe is created, which is flanked by side lobes, due to limitations (e.g., inherent laser limitations, internal reflection in the cuvette caused by imperfections, chips or scratches, debris/dust/fuzz on the cuvette, inside, or outside wall, and dust on the excitation optics) of the cytometer system At operation 604, relatively small and large particles are flowed through a flow path. Relatively small particles can be, for example, as small as 50 nm while relatively large particles can be as large as 50 µm particles, which is a dynamic range of 1000×. A detection system monitors for energy signals (fluorescence and/or scatter) resultant from particles interfacing with the light pattern of lobes. Generally, the center lobe provides greater energy than the shown side lobes. Hence, a relatively small particle will trigger a given threshold only when excited by the center lobe, while a relatively large particle will trigger the same threshold when passing through a side and center lobes, thus, causing potential measurement errors.

At operation 606, a first signal is detected that has an energy level exceeding a first threshold. The first threshold can be set low enough to detect a relatively small sized particle passing through the main lobe.

At operation 608, a second signal is detected (successively after the first signal) that has an energy level exceeding a second threshold that is higher than the first threshold. The second threshold can be set at a level to detect a relatively large particle passing through the main lobe. Hence, a small particle would not trigger the second threshold. If the second threshold was not triggered by the second signal, the particle would be processed as a small particle.

With both thresholds being triggered, it is still unknown whether the triggers occurred from a single large particle passing through multiple lobes, or from a large particle passing through a side lobe directly following a small particle passing through a main lobe. Accordingly, at operation 610, the detection system analyzes whether the second signal was received at a predetermined time after the first signal according to the time of particle flight between adjacent lobes. A large particle would trigger at a side lobe and main lobe between an expected time differential, since the flow rate and distance between lobes are both constant. While different particles would more than likely be separated at a distance that is not exactly coincident with the distance between lobes.

When it is determined that the first and second signals are resultant from a relatively large particle according to the time information, a requisite integration is performed to measure characteristics of the large particle at operation 612. When it is determined that the first and second signals are resultant from a relatively large particle directly following a relatively small particle, requisite integrations are performed to measure characteristics of the both particles at operation 614.

Figure 6B:
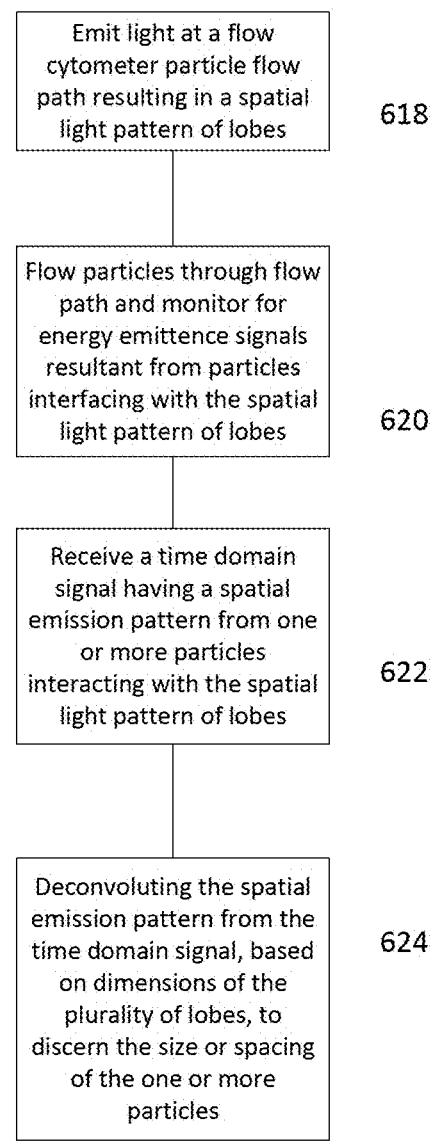

FIG. 6B shows a method 616 for detecting a particle using any of the systems disclosed herein. At operation 618, laser light is emitted at a flow cytometer particle flow path resulting in a spatial light pattern of lobes. Generally, a main center lobe is created, which is flanked by side lobes, due to limitations (e.g., inherent laser limitations, internal reflection in the cuvette caused by imperfections, chips or scratches, debris/dust/fuzz on the cuvette, inside, or outside wall, and dust on the excitation optics) of the cytometer system At operation 620, relatively small and large particles are flowed through a flow path. Relatively small particles can be, for example, as small as 50 nm while relatively large particles can be as large as 50 µm particles, which is a dynamic range of 1000×. A detection system monitors for energy signals (fluorescence and/or scatter) resultant from particles interfacing with the light pattern of lobes.

At operation 622, a time domain signal having a spatial emission pattern is detected from one or more particles interacting with the plurality of lobes. However, size of the one or more particles is not discernible in the emission pattern due to convolution between the spatial light pattern (plurality of lobes) of the laser and the spatial emission pattern of the particle.

At operation 624, the spatial emission pattern is deconvoluted (e.g., using a deconvolution filter as described above) from the time domain signal, based on dimensions of the plurality of lobes, to discern the size or spacing of the one or more particles.

FIG. 7 is a high level block diagram of a computing system 700 that may be used to implement any of the entities or components described above, which may include one or more of the subsystems or components shown in FIG. 5. The subsystems shown in FIG. 5 are interconnected via a system bus 705. Additional subsystems such as a printer 710, keyboard 715, fixed disk 720, monitor 725, which is coupled to display adapter 730, and others are shown. Peripherals and input/output (I/O) devices, which couple to an I/O controller 735, can be connected to the computing apparatus 700 by any number of means known in the art, such as port 740 (e.g., USB, serial, etc.) For example, port 740 or external interface 745 can be used to connect the computing apparatus 700 to a wide or local area network, the Internet, a mouse input device, or any of the subsystems shown at FIG. 5 for control thereof. The interconnection via the system bus 705 allows the central processor 750 to communicate with each subsystem and to control the execution of instructions from system memory 755 or the fixed disk 720, as well as the exchange of information between subsystems. The system memory 755 and/or the fixed disk 720 may embody a computer readable medium.

It should be understood that the present invention as described above can be implemented in the form of control logic using computer software in a modular or integrated manner. Based on the disclosure and teachings provided herein, a person of ordinary skill in the art can know and appreciate other ways and/or methods to implement the present invention using hardware and a combination of hardware and software.

Any of the software components, user interfaces, or methods described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

What is claimed is:

1. A method for particle detection comprising:
   directing a light source at a flow path of particles of a flow cytometer, wherein the particles comprise first particles and second particles, wherein the second particles are larger than the first particles, and wherein the directed light results in a light pattern having a plurality of lobes in the flow path;
   detecting a first signal exceeding a first threshold, wherein the first signal is caused by the particles flowing through a first lobe of the plurality of lobes of the light pattern;
   detecting a second signal exceeding a second threshold, wherein the second signal is caused by the particles flowing through a second lobe of the plurality of lobes of the light pattern, and wherein the second threshold is greater than the first threshold; and based on detecting the second signal and detecting the first signal at different times, determining that the first and second signals were created by a particle of the second particles.

2. The method of claim 1, further comprising determining that the second signal was received at a predetermined time after the first signal according to particle travel speed between adjacent lobes of the plurality of lobes.

3. The method of claim 1, further comprising resetting one or more integrators configured to process a particle of the first particles or to process a particle of the second particles.

4. The method of claim 1, wherein the second particles are up to 1000 times larger than the first particles.

5. The method of claim 1, wherein the first and second signals are detected by an analog logic system.

6. The method of claim 1, wherein the first threshold is set according to an energy emission level of a particle of the first particles.

7. The method of claim 6, wherein the second threshold is set according to an energy emission level of a particle of the second particles.

8. A particle detection system comprising:
a cytometer system configured for directing light source at a flow path of particles, wherein the particles comprise first particles and second particles, wherein the second particles are larger than the first particles, and wherein the light results in a light pattern having a plurality of lobes in the flow path; and
a detection system configured for:
  detecting a first signal exceeding a first threshold, wherein the first signal is caused by the particles flowing through a first lobe of the plurality of lobes of the light pattern;
  detecting a second signal exceeding a second threshold, wherein the second signal is caused by the particles flowing through a second lobe of the plurality of lobes of the light pattern, and wherein the second threshold is greater than the first threshold; and
  based on detecting the second signal and detecting the first signal at different times, determining one of the first and second signals were created by a particle of the second particles.

9. The system of claim 8, wherein the detection system is further configured for determining whether the second signal was received at a predetermined time after the first signal according to particle travel speed between adjacent lobes of the plurality of lobes.

10. The system of claim 8, wherein the second particles are up to 1000 times larger than the first particles.

11. The system of claim 8, wherein the detection system is configured to set the first threshold based on an energy emission level of a particle of the first particles.

12. The system of claim 11, wherein the detection system is configured to set the second threshold based on an energy emission level of a particle of the second particles.

13. The system of claim 8, wherein the detection system comprises an analog logic system.

14. The system of claim 13, wherein the analog logic system comprise plurality of comparators.

* * * * *